United States Patent [19]

Yamada et al.

[11] Patent Number: 4,985,409

[45] Date of Patent: Jan. 15, 1991

[54] ADENOSINE DERIVATIVES AND PHARMACEUTICAL COMPOSITION THEREOF

[75] Inventors: Toshio Yamada; Ken-ichi Kageyama, both of Hyogo, Japan

[73] Assignee: Nippon Zoki Pharmaceutical Co., Ltd., Osaka, Japan

[21] Appl. No.: 462,246

[22] Filed: Jan. 9, 1990

[30] Foreign Application Priority Data

Jan. 11, 1989 [JP] Japan .................................... 1-5658

[51] Int. Cl.$^5$ ..................... A61K 31/70; C07H 19/167

[52] U.S. Cl. ........................................ 514/46; 536/24; 536/26

[58] Field of Search ...................... 514/45, 46; 536/24, 536/26

[56] References Cited

U.S. PATENT DOCUMENTS

| | | | |
|---|---|---|---|
| 3,471,472 | 10/1969 | Thiel et al. | 536/26 |
| 3,838,147 | 9/1974 | Pohlke et al. | 536/26 |
| 3,845,035 | 10/1974 | Kampe et al. | 536/26 |
| 3,922,261 | 11/1975 | Pohlke et al. | 536/26 |
| 4,501,735 | 2/1985 | Trivedi et al. | 514/46 |
| 4,614,732 | 9/1986 | Hamilton et al. | 514/46 |
| 4,616,003 | 10/1986 | Hamilton et al. | 514/46 |
| 4,626,526 | 12/1986 | Bristol | 514/46 |
| 4,657,897 | 4/1987 | Bristol et al. | 514/47 |
| 4,657,898 | 4/1987 | Bristol et al. | 514/47 |
| 4,663,313 | 5/1987 | Bristol et al. | 514/46 |
| 4,683,223 | 7/1987 | Trivedi | 514/46 |
| 4,791,103 | 12/1988 | Trivedi et al. | 514/46 |
| 4,837,207 | 6/1989 | Trivedi | 514/46 |
| 4,843,066 | 6/1989 | Yamada et al. | 514/45 |

OTHER PUBLICATIONS

Goodman, "Chemical Syntheses and Transformations of Nucleosides", in Basic Principles in Nucleic Acid Chemistry, P.O.P.Ts'O ed., Academic Press, New York, 1974, see p. 144.

Kikugawa et al., J. Med. Chem., 16(4), 358-364 (1973).

*Primary Examiner*—Johnnie R. Brown

*Assistant Examiner*—L. Eric Crane

*Attorney, Agent, or Firm*—Armstrong, Nikaido, Marmelstein, Kubovcik & Murray

[57] ABSTRACT

The present invention relates to novel adenosine derivatives having the formula (I):

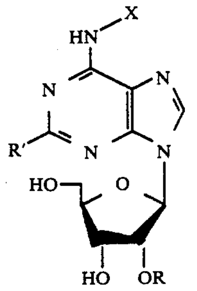

(I)

wherein R is a lower alkyl group; R' is hydrogen or a lower alkyl group; X is a cycloalkyl group, an alkyl group having at least one hydroxy group, an alkyl group having at least one phenyl group, a bicycloalkyl group, a naphthylalkyl group, an acenaphthylenylalkyl group or a group of the formula (II) or (III);

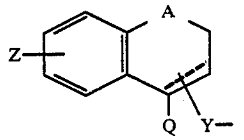

(II)

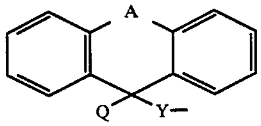

(III)

Z is hydrogen, a hydroxy group or a lower alkoxy group, Q is hydrogen or a hydroxy group, A is $-CH_2-$, $-O-$, $-S-$ or shows a direct connection; Y is $-(CH_2)_n-$ or shows a direct connection; n is an integer of 1 to 3; and the broken line is a double bond or a single bond.

and pharmaceutically acceptable salt thereof, which are useful as antihypertensive agents.

4 Claims, 1 Drawing Sheet

-----: Control

—○—: $N^6$-(2,3-dihydro-1H-indene-1-yl)adenosine

—●—: Compound 11

ADENOSINE DERIVATIVES AND PHARMACEUTICAL COMPOSITION THEREOF

BACKGROUND OF THE INVENTION

The present invention relates to novel adenosine derivatives, pharmaceutically acceptable salts thereof and pharmaceutical compositions containing them as an active ingredient.

Hypertension is one of the most serious risk factors causing cerebral apoplexy and cardiopathy which are included in the major causes of death. Thus various antihypertensive agents such as diuretics, sympathetic depressant drugs, direct-acting vasodilators, calcium antagonists or angiotensin antagonists have been developed and used for treatment of hypertension. However, for example, side effects such as bradycardia causing various symptoms such as tiredness, depression of activity, disturbance of cerebral circulation or cerebral ischemia are sometimes observed under the treatment with sympathetic depressant drugs. Therefore, the developments of antihypertensive agents having greater safety and effectiveness are desired. As a result of investigations for orally administrable antihypertensive compounds, the inventors have found adenosine derivatives having vasodilatively hypotensive effect.

SUMMARY OF THE INVENTION

An object of the present invention is to provide novel adenosine derivatives and pharmaceutically acceptable salts thereof having an excellent antihypertensive effect. Another object of the present invention is to provide pharmaceutical compositions containing these adenosine derivatives or pharmaceutically acceptable salts thereof as an active ingredient.

DETAILED DESCRIPTION OF THE INVENTION

Figure 1:
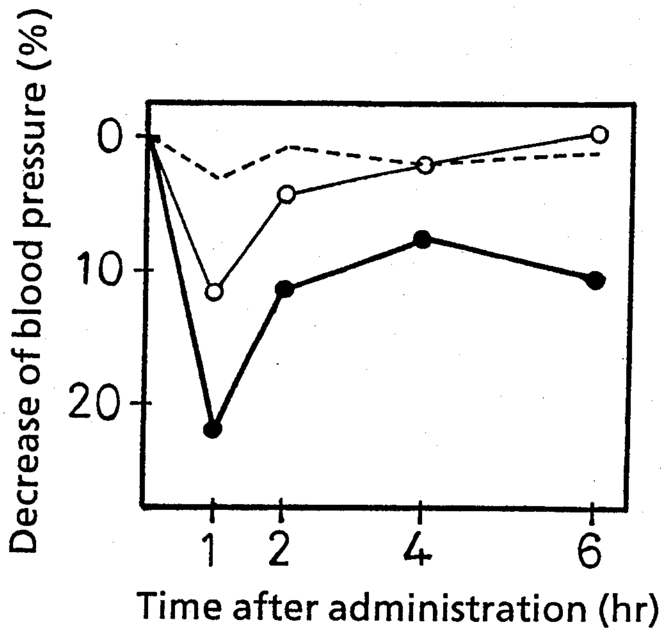
FIG. 1 shows a result of hypotensive activity of the present invention compared to another adenosine derivative.

The adenosine derivatives of the present invention are represented by the following formula (I):

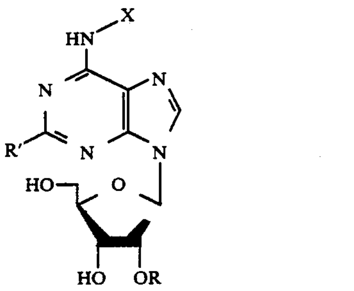
(I)

wherein R is a lower alkyl group; R' is hydrogen or a lower alkyl group; X is a cycloalkyl group, an alkyl group having at least one hydroxy group, an alkyl group having at least one phenyl group, a bicycloalkyl group, a naphthylalkyl group, an acenaphthylenylalkyl group or a group of the formula (II) or (III);

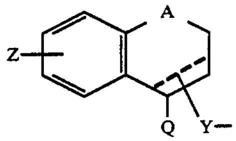
(II)

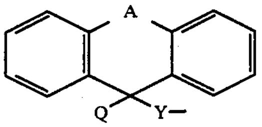
(III)

Z is hydrogen, a hydroxy group or a lower alkoxy group, Q is hydrogen or a hydroxy group, A is $-CH_2-$, $-O-$, $-S-$ or shows a direct connection; Y is $-(CH_2)_n-$ or shows a direct connection; n is an integer of 1 to 3; and the broken line is a double bond or a single bond.

In the above formula (I), R represents a lower alkyl group, preferably a straight or branched alkyl group having 1 to 3 carbon atoms, such as methyl, ethyl, propyl or isopropyl. R' represents hydrogen or a lower alkyl group, preferably a straight or branched alkyl group having 1 to 3 carbon atoms, such as methyl, ethyl, propyl or isopropyl.

X represents a cycloalkyl group, preferably a cycloalkyl group having 3 to 8 carbon atoms, such as cyclopropyl, cyclobutyl, cyclopentyl, cyclohexyl, cycloheptyl or cyclooctyl; an alkyl group having at least one hydroxy group, preferably a straight or branched alkyl group having 1 to 4 carbon atoms, such as methyl, ethyl, propyl, isopropyl, butyl, isobutyl, sec-butyl or tert-butyl having one or two hydroxy groups; an alkyl group having at least one phenyl group, preferably a phenylalkyl group or a diphenylalkyl group, for example, a straight or branched alkyl group having 1 to 3 carbon atoms, such as methyl, ethyl, propyl or isopropyl having one or two phenyl groups; a bicycloalkyl group, preferably endo- or exo-bicyclo[2,2,1]heptyl group; a naphthylalkyl group, preferably an alkyl group having 1 to 3 carbon atoms, such as methyl, ethyl, propyl or isopropyl having a naphthyl group; an acenaphthylenylalkyl group including 1,2-dihydro form thereof, preferably an alkyl group having 1 to 3 carbon atoms, such as methyl, ethyl, propyl or isopropyl having a acenaphthylenyl group; or a group of the above formula (II) or (III).

In the formulas (II) and (III), Z represents hydrogen, a hydroxy group or a lower alkoxy group, preferably a straight or branched alkoxy group having 1 to 3 carbon atoms, such as methoxy, ethoxy, propoxy or isopropoxy. Q represents a hydrogen or a hydroxy group. A is $-CH_2-$, $-O-$, $-S-$ or shows a direct connection. Y is $-(CH_2)_n-$ or shows a direct connection. n is an integer of 1 to 3, and the broken line represents a double bond or a single bond.

The adenosine derivatives of the present invention include pharmaceutically acceptable salts of the compounds having above formula (I), for example, salts with alkali metal such as sodium or potassium, with alkaline-earth metal such as calcium or barium, or with other metals such as aluminum, or salts as acid addition with an acid such as hydrochloric acid, sulfuric acid, nitric acid, phosphoric acid, formic acid, acetic acid, citric acid or lactic acid, or salts with an organic base such as ammonia or the like. These salts can be prepared from free adenosine derivatives or other salts of these derivatives by a known method.

When optical isomers exist in the compounds of the invention, the present invention includes any of the dl, d and l-isomers.

The adenosine derivatives of the present invention can be prepared as follows.

(1) Both 3'-O- and 5'-O-positions of an adenosine derivative are protected by tetraisopropyldisiloxane (TIPDS) group to carry out O-alkylation selectively at the 2'-O-position. A 6-Chloropurine-9-riboside and TIPDS·$Cl_2$ (1,3-dichloro-1,1,3,3-tetraisopropyldisiloxane dichloride) are stirred for several hours at room temperature to protect 3'-O- and 5'-O-positions, and then 2'-O-position of the compound protected by TIPDS can be selectively alkylated by an alkylating agent such as methyl iodide, ethyl iodide, propyl iodide or butyl iodide in the presence of catalyst such as silver oxide.

After the 2'-O-alkylation, a group of —NH—X is introduced to 6-position of the purine by using an amine (X—$NH_2$) containing the group X in the formula (I) according to a conventional method. The protecting group, TIPDS, can be removed before or after this replacement reaction between the amine and chloro group at 6-position of the purine of adenosine.

(2) The compound of the present invention can be produced by alkylation of an adenosine derivative corresponding to the compound represented by the formula (I), in which R is hydrogen, by an alkylating agent. A diazoparaffin, such as diazomethane, diazoethane or diazopropane, can be used as the alkylating agent. The appropriate solvent which does not inhibit the reaction such as 1,2-dimethoxyethane can be preferably used. This O-alkylating reaction can be carried out as follows:

(i) The reaction mixture is reacted for several minutes to several hours at room temperature in the presence of a catalyst such as p-toluenesulfonic acid.

(ii) The starting material is dissolved in about 80° C. hot water and an alkylating agent such as diazoparaffin is added thereto, and the reaction mixture is reacted for several hours to a day.

The resulting compounds of the present invention can be purified by known methods such as distillation chromatography and recrystallization. Identification is established through, inter alia, melting point (m.p.), elemental analysis, IR, NMR, UV, mass spectrum, etc.

EXAMPLE

The following examples, which are illustrative only and not intended to limit the scope of the invention, describe the preparation of the compounds of the present invention.

EXAMPLE 1

(i) 500 ml of acetic anhydride and 500 ml of pyridine were added to 100 g of inosine, and the reaction mixture was stirred for 4 to 10 hours at room temperature. After concentration under reduced pressure, the precipitated crystalline was separated by filtration, washed with water and dried to give 132 g of 2',3',5'-O)-triacetylinosine (yield: 98%)

(ii) 50 g of 2', 3',5'-O-triacetylinosine was dissolved in 400 ml of chloroform. 30 ml of thionyl chloride and 7.2 ml of dimethylformamide were added, and the solution was refluxed with heating for 2 to 4 hours. The reaction mixture was poured into ice cold water, and the separated chloroform layer was washed with saturated aqueous solution of sodium hydrogencarbonate and brine. After drying over sodium sulfate anhydride, the solvent was distilled off. The residue was dissolved in 20% ammonia methanol solution and the container was sealed. After stirring for 3 to 5 hours, the solution was concentrated under reduced pressure. The precipitated crystalline was separated by filtration and dried to give 6-chloro-9-β-D-ribofuranosyl-9H-purine (yield: 60%).

(iii) 20 g of 6-chloro-9-β-D-ribofuranosyl-9H-purine was dissolved in 350 ml of pyridine. 26 g of TIPDS·$Cl_2$ was added thereto and the solution was stirred for 1 to 4 hours at room temperature. The solution was concentrated to dryness and the residue was suspended in water. Benzene was added thereto to extract the resulting product. The benzene layer was washed with 0.1N hydrochloric acid aqueous solution, saturated aqueous solution of sodium hydrogencarbonate and brine. After drying over sodium sulfate anhydride, the solvent was distilled off. The residue was recrystallized from n-hexane to give 24 g of 6-chloro-9-(3',5'-O-TIPDS-β-D-ribofuranosyl)-9H-purine (yield: 65%).

(iv) 20 g of the resulting product was dissolved in 300 ml of benzene and 200 ml of ethyl iodide, and silver oxide were added thereto to carry out methylation. After reacting for 4 to 10 hours, silver oxide and silver iodide were filtered off and the crude product was purified by silica gel column chromatography to give 6-chloro-9-(2'-O-methyl-3'5'-O-TIPDS-β-D-ribofuranosyl)-9H-purine (yield: 75%).

(v) 16.3 g of the resulting product was dissolved in tetrahydrofuran and 66 ml of 1M solution of tetrabutylammonium fluoride was added. The reaction mixture was stirred for several minutes. The solvent was distilled off and the residue was purified by silica gel column chromatography to give 6-chloro-9-(2'-O-methyl-β-D-ribofuranosyl)-9H-purine.

(vi) To 1.5 g of 6-chloro-9-(2'-O-methyl-β-D-ribofuranosyl)-9H-purine and 510 mg of cyclopentylamine, 1.5 ml of triethylamine and 70 ml of ethanol were added. The solution was refluxed with heating for several ten minutes to 8 hours. After washing the residue with water, methanol was added and the solution was concentrated to dryness again. The residue was recrystallized with ethyl acetate to give $N^6$-cyclopentyl-2'-O-methyladenosine (Compound 1).

yield: 80%

NMR($D_2O$): δ=1.57(4H,m), 1.72(2H,m), 1.94(2H,m), 3.36(3H,s), 3.58(1H.m), 3.70(1H,m), 4.00(1H,m), 4.35(2H,m), 4.53(1H,m), 5.27(1H,d,J=5.37Hz), 5.45(1H,m), 6.02(1H,d,J=5.86Hz), 7.78(1H,m), 8.21(1H,s), 8.39(1H,s)

In the same manner as mentioned above, the following compounds were obtained.

$N^6$-cyclohexyl-2'-O-methyladenosine (Compound 2) NMR($D_2O$): δ=1.33(4H,m), 1.61(2H,m), 1.74(2H,m), 1.87(2H,m), 3.30(3H,s), 3.55(1H,m), 3.67(1H,m), 3.97(1H,m), 4.09(1H,m), 4.34(2H,m), 5.25(1H,d,J=4.88Hz), 5.43(1H,m), 6.00(1H,d,J=5.86Hz), 7.65(1H,m), 8.19(1H,s), 8.37(1H,s)

$N^6$-(2,3-dihydroxypropyl)-2'-O-methyladenosine (Compound 3) NMR($D_2O$): δ=3.42(3H,s), 3.53(1H,m), 3.61(2H,m), 3.70(1H,dd,J=1.95, 12.7Hz), 3.81(1H,m), 3.90(1H,m), 3.98(1H,m), 4.26(1H,m), 4.41(1H,dd,J=5.37,6.35Hz), 4.56(1H,m), 6.01(1H,d,J=6.35Hz), 8.07(1H,s), 8.20(1H,s)

$N^6$-benzyl-2'-O-methyladenosine (Compound 4)

NMR($D_2O$): δ=3.32(3H,s), 3.57(1H,m), 3.69(1H,m), 4.00(1H,m), 4.37(2H,m), 4.72(2H,brs), 5.30(1H,d,J=5.4Hz), 5.43(1H,m), 6.04(1H,d,J=5.9Hz), 7.2–7.5(5H,m), 8.22(1H,s), 8.43(1H,s), 8.43(1H,s), 8.51(1H,s)

$N^6$-(2,2-diphenylethyl)-2'-O-methyladenosine (Compound 5)

m.p.: 173.5°-175 ° C.

NMR($D_2O$): δ=3.30(3H,s), 3.56(1H,m), 3.66(1H,m), 3.97(1H,m), 4.12(2H,m), 4.34(2H,m), 4.59(1H.m), 5.25(1H,d,J=3.42Hz), 5.35(1H,t,J=5.37Hz), 5.99(1H,d,J=5.86Hz), 7.10-7.40(10H,m), 7.84(1H,m), 8.28(1H,s), 8.33(1H,s)

$N^6$-(exo-dicyclo[2,2,1]heptyl)-2'-O-methyladenosine (Compound 6)

NMR($D_2O$): δ=1.10–1.40(4H,m), 1.45(2H,m), 1.64(2H,m), 2.23(2H,m), 3.31(3H,s), 3.57(1H,m), 3.67(1H,m), 3.99(1H,m), 4.38(3H,m), 5.30(1H,d,J=4.9Hz), 5.47(1H,m), 6.02(1H,d,J=5.9Hz), 7.68(1H,d,J=7.3Hz), 8.25(1H,s), 8.40(1H,s)

$N^6$-(endo-dicyclo[2,2,1]heptyl)-2'-O-methyladenosine (Compound 7)

NMR($D_2O$): δ=1.20–1.50(6H,m), 1.64(1H,m), 1.91(1H,m), 2.18(1H,m), 2.52(1H,m), 3.32(3H,s), 3.59(1H,m), 3.69(1H,m), 4.01(1H,m), 4.37(3H,m), 5.31(1H,d,J=4.7Hz), 5.47(1H,m), 6.02(1H,d,J=5.9Hz),7.88(1H,s), 8.23(1H,s), 8.42(1H,s)

$N^6$-(1-naphthyl)methyl-2'-O-methyladenosine (Compound 8)

m.p.: 184.5°-185.5 ° C.

NMR($D_2O$): δ=3.32(3H,s), 3.56(1H,m), 3.69(1H,m), 3.99(1H,m), 4.35(1H,m), 4.39(1H,m), 5.20(2H,m), 5.27(1H,d,J=4.88Hz), 5.37(1H,m), 6.04(1H,d,J=6.35Hz), 7.44(2H,m), 7.55(2H,m), 7.81(1H,d,J=9.28Hz), 7.94(1H,d,J=9.28Hz), 8.22(2H,m), 8.43(1H,s), 8.50(1H,m)

$N^6$-(1-acenaphthylenyl)methyl-2'-O-methyladenosine (Compound 9)

NMR($D_2O$): δ=3.36(3H,s), 3.58(1H,m), 3.70(1H,m), 4.00(1H,m), 4.36(1H,m), 4.40(1H,m), 5.00(2H,m), 5.29(1H,d,J=5.4Hz), 5.41(1H,m), 6.05(1H,d,J=6.8Hz), 7.63(1H,d,J=6.4Hz), 7.80(1H,d,J=7.8Hz), 7.87(1H,d,J=8.3Hz), 7.91(1H,d,J=6.4Hz), 8.28(1H,s), 8.44(1H,s), 8.52(1H,m)

$N^6$-(1,2-dihydro-1-acenaphthylenyl)methyl-2'-O-methyladenosine (Compound 10)

NMR($D_2O$): δ=3.33(3H,s), 3.47(2H,m), 3.60(1H,m), 3.69(2H,m), 3.94(1H,m), 4.01(1H,m), 4.16(1H,m), 4.36(1H,m), 4.40(1H,m), 5.29(1H,d,J=5.4Hz), 5.41(1H,m), 6.04(1H,d,J=5.9Hz), 7.34(1H,m), 7.47(1H,t,J=7.8Hz), 7.65(1H,t,J=8.8Hz), 8.27(2H,m), 8.44(1H,s)

$N^6$-(2,3-dihydro-1H-indene-1-yl)-2'-O-methyladenosine (Compound 11)

NMR($D_2O$): δ=2.12(1H,m), 2.48(1H,m), 2.85(1H,m), 3.02(1H,m), 3.33(3H,m), 3.59(1H,m), 3.69(1H,m), 4.00(1H,m), 4.38(2H,m), 5.31(1H,d,J=4.39Hz), 5.44(1H,t,J=5.37Hz), 5.92(1H,m), 6.04(1H,d,J=5.86Hz), 7.10–7.30(4H,m), 8.17(1H,m), 8.28(1H,s), 8.41(1H,s)

$N^6$-(2,3-dihydro-1H-indene-2-yl)-2'-O-methyladenosine (Compound 12)

m.p.: 139°-141° C.

NMR($D_2O$): δ=3.02(2H,m), 3.27(2H,m), 3.31(3H,s), 3.56(1H,m), 3.68(1H,m), 3.99(1H,m), 4.35(2H,m), 4.97(1H,m), 5.30(1H,m), 5.42(1H,m), 6.02(1H,d,J=5.86Hz), 7.14(2H,m), 7.22(2H,m), 8.12(1H,m), 8.26(1H,s), 8.40(1H,s)

$N^6$-(2,3-dihydro-1H-indene-1-yl)methyl-2'-O-methyladenosine (Compound 13)

NMR($D_2O$): δ=1.89(1H,m), 2.16(1H,m), 2.78(1H,m), 2.92(1H,m), 3.33(1H,s), 3.58(3H,m), 3.70(1H,m), 3.84(1H,m), 4.01(1H,m), 4.38(2H,m), 5.29(1H,d,J=4.9Hz), 5.43(1H,m), 6.04(1H,d,J=6.4Hz), 7.14(1H,m), 7.23(1H,m),7.29(1H,m), 8.08(1H,m), 8.25(1H,s), 8.42(1H,s)

$N^6$-(3H-indene-1-yl)methyl-2'-O-methyladenosine (Compound 14)

NMR($D_2O$): δ=3.32(3H,s), 3.32(2H,m), 3.57(1H,m), 3.69(1H,m), 4.00(1H,m), 4.36(1H,m), 4.39(1H,m),4.69(2H,m), 5.29(1H,d,J=4.9Hz), 5.41(1H,m), 6.03(1H,d,J=5.9Hz), 6.35(1H,m), 7.19(1H,t,J=7.3Hz), 7.27(1H,t,J=7.3Hz), 7.46(1H,d,J=7.3Hz), 7.52(1H,d,J=7.3Hz), 8.25(1H,s), 8.34(1H,s), 8.42(1H,s) $N^6$-(5-methoxy-2,3-dihydro-1H-indene-1-yl)-2'-O-methyladenosine (Compound 15)

NMR($D_2O$): δ=2.14(1H,m), 2.51(1H,m), 2.81(1H,m), 3.01(1H,m), 3.33(1H,s), 3.57(1H,m), 3.70(1H,m), 3.72(3H,s), 4.00(1H,m), 4.37(1H,m), 4.40(1H,m), 5.27(1H,d,J=4.9Hz), 5.42(1H,m), 5.85(1H,m), 6.04(1H,d,J=5.9Hz), 6.69(1H,dd,J=1.9, 8.8Hz), 6.83(1H,d,J=1.9Hz), 7.09(1H,m), 8.08(1H,m), 8.28(1H,s), 8.40(1H,s)

$N^6$-(1-tetrahydronaphthyl)-2'-O-methyladenosine (Compound 16)

m.p.: 174°-174.3 ° C.

NMR($D_2O$): δ=1.77(1H,m), 2.01(3H.m), 2.77(2H,m), 3.34(3H,s), 3.59(1H,m), 3.69(1H,m), 4.00(1H,m), 4.33(1H,s), 4.41(1H,m), 5.28(1H,d,J=5.37HZ), 5.42(1H,m), 5.64(1H,m), 6.04(1H,d,J=5.86Hz), 7.11(4H,m), 8.11(1H,m), 8.27(1H,s), 8.40(1H,s)

$N^6$-(2-tetrahydronaphthyl)-2'-O-methyladenosine (Compound 17)

m.p.: 124.5°-125 ° C.

NMR($D_2O$): δ=1.85(1H,m), 2.09(1H,m), 2.89(3H,m), 3.08(1H,m), 3.32(1H,m), 3.58(1H,m), 3.68(1H,m), 3.99(1H,m), 4.34(1H,m), 4.37(1H,m), 4.51(1H,m), 5.26(1H,d,J=4.88Hz), 5.40(1H,m), 6.02(1H,d,J=5.86Hz), 7.09(4H,m), 7.86(1H,m), 8.23(1H,s), 8.40(1H,s)

$N^6$-(3,4-dihydro-1-naphthyl)methyl-2'-O-methyladenosine (Compound 18)

NMR($D_2O$): δ=2.20(2H,m), 2.68(2H,t,J=7.8Hz), 3.33(3H,s), 3.70(1H,m), 4.01(1H,m), 4.37(1H,m), 4.40(1H,m), 4.54(2H,m), 5.29(1H,d,J=4.9Hz), 5.43(1H,m), 5.98(1H,m), 6.04(1H,d,J=5.9Hz), 7.16(3H,m), 7.35(1H,m), 8.07(1H,m), 8.27(1H,s), 8.42(1H,s)

$N^6$-(5-hydroxy-1-tetrahydronaphthyl)-2'-O-methyladenosine (Compound 19)

NMR($D_2O$): δ=1.73(1H,m), 1.94(3H,m), 2.55(2H,m), 3.33(3H,s), 3.57(1H,m), 3.69(1H,m), 4.00(1H,m), 4.36(1H,m), 4.40(1H,m), 5.27(1H,d,J=5.4Hz), 5.41(1H,m), 5.60(1H,m), 6.03(1H,d,J=5.9Hz), 6.64(2H,m), 6.88(1H,t,J=8Hz), 7.99(1H,m), 8.26(1H,s), 8.39(1H,s), 9.24(1H,s)

$N^6$-(1-hydroxy-1-tetrahydronaphthyl)methyl-2'-O-methyladenosine (Compound 20)

NMR($D_2O$): δ=1.68(1H,m), 1.77(1H,m), 1.86(1H,m), 1.99(1H,m), 2.74(2H,m), 3.33(3H,s), 3.57(2H,m), 3.70(1H,m), 4.00(2H,m), 4.38(2H,m), 5.30(1H,d,J=4.9HZ), 5.39(1H,m), 5.66(1H,m), 6.04(1H,d,J=5.9Hz), 7.07(1H,m), 7.16(2H,m), 7.37(1H,m), 7.60(1H,m), 8.24(1H,s), 8.45(1H,s)

$N^6$-(5-methoxy-1-tetrahydronaphthyl)-2'-O-methyladenosine (Compound 21)

NMR($D_2O$): δ=1.73(1H,m), 1.94(3H,m), 2.63(2H,m), 3.34(3H,s), 3.59(1H,m), 3.70(1H,m),3.78(3H,s), 4.01(1H,m), 4.37(1H,m), 4.40(1H,m), 5.28(1H,d,J=5.4Hz), 5.41(1H,m), 5.63(1H,m), 6.04(1H,d,J=5.9Hz), 6.79(1H,m), 6.80(1H,d,J=8.3Hz), 7.07(1H,t,J=8.3Hz), 8.05(1H,m), 8.27(1H,s), 8.40(1H,s)

$N^6$-(6-methoxy-1-tetrahydronaphthyl)-2'-O-methyladenosine (Compound 22)

NMR($D_2O$): δ=1.74(1H,m), 1.97(3H,m), 2.74(2H,m), 3.34(3H,s), 3.57(1H,m), 3.70(3H,s), 3.70(1H,m), 4.01(1H,m), 4.36(1H,m), 4.39(1H,M), 5.27(1H,d,J=5.9Hz), 5.42(1H,m), 5.56(1H,m), 6.04(1H,d,J=5.9Hz), 6.66(1H,m), 6.68(1H,m), 7.07(1H,m), 7.96(1H,m), 8.27(1H,s), 8.39(1H,s)

$N^6$-(7-methoxy-1-tetrahydronaphthyl)-2'-O-methyladenosine (Compound 23)

NMR($D_2O$): δ=1.74(1H,m), 1.96(3H,m), 2.70(2H,m), 3.34(3H,s), 3.60(3H,s), 3.58(1H,m), 3.70(1H,m), 4.00(1H,m), 4.37(1H,m), 4.40(1H,m), 5.28(1H,d,J=5.4Hz), 5.40(1H,m), 5.58(1H,m), 6.04(1H,d,J=5.9Hz), 6.71(1H,m), 6.76(1H,dd,J=2.9, 8.7Hz), 7.03(1H,d,J=8.7Hz), 8.09(1H,m), 8.28(1H,s), 8.41(1H,s)

$N^6$-(4-chromanyl)-2'-O-methyladenosine (Compound 24) m.p.: 196°-196.2 ° C.

NMR($D_2O$): δ=2.16(2H,m), 3.33(3H,m), 3.56(1H,m), 3.70(1H,m), 3.99(1H,m), 4.23(1H,m), 4.35(3H,m), 5.28(1H,d,J=4.88Hz), 5.39(1H,m), 5.69(1H,m), 6.04(1H,d,J=5.86Hz), 6.79(2H,m), 7.13(2H,m), 8.29(2H,m), 8.43(1H,s)

$N^6$-(4-thiochromanyl)-2'-O-methyladenosine (Compound 25)

NMR($D_2O$): δ=2.24(1H,m), 2.32(1H,m), 3.13(1H,m), 3.18((1H,m), 3.33(3H,s), 3.57(1H,m), 3.69(1H,m), 3.99(1H,m), 4.35(1H,m), 4.39(1H,m), 5.27(1H,d,J=5.4Hz), 5.37(1H,m), 5.64(1H,m), 6.04(1H,d,J=5.9Hz), 6.99(1H,m), 7.12(1H,m), 7.19(1H,m), 8.26(1H,s), 8.35(1H,s), 8.43(1H,s)

$N^6$-(9-fluorenyl)-2'-O-methyladenosine (Compound 26) m.p.: 189°-190° C.

NMR($D_2O$): δ=3.35(3H,s), 3.59(1H,m), 3.71(1H,m), 4.01(1H,m), 4.37(1H,m), 4.42(1H,m), 5.29(3H,m), 5.38(1H,m), 6.06(1H,d,J=6.35Hz), 7.28(2H,t,J=7.81Hz), 6.69(1H,m), 7.41(2H,t,J=7.81Hz), 7.49(2H,m), 7.86(2H,d,J=7.32Hz), 8.42(1H,s), 8.47(1H,s)

$N^6$-(9-fluorenyl)methyl-2'-O-methyladenosine (Compound 27) NMR($D_2O$): δ=3.35(3H,s), 3.53(1H,m), 3.63(1H,m), 3.95(2H,m), 4.21(1H,m), 4.30(2H,m), 5.27(1H,d,J=3.9Hz), 5.35(1H,m), 5.96(1H,d,J=5.2Hz), 6.61(1H,d,J=7.3Hz), 7.02(2H,t,J=7.3Hz), 7.20(2H,t,J=7.3Hz), 7.47(1H,d,J=7.3Hz), 7.67(1H,d,J=7.3Hz), 7.81(1H,d,J=7.3Hz), 7.94(1H,d,J=7.3Hz), 8.08(1H,s), 8.33(1H,s)

$N^6$-(9-hydroxy-9-fluorenyl)methyl-2'-O-methyladenosine (Compound 28)

NMR($D_2O$): δ=3.37(3H,s), 3.58(1H,m), 3.67(1H,m), 3.99(3H,m), 4.37(2H,m), 5.29(1H,d,J=4.9Hz), 5.37(1H,t,J=5.4Hz), 6.02(1H,d,J=6.4Hz), 6.40(1H,s), 7.24(2H,m), 7.35(2H,t,J=7.3Hz), 7.53(2H,d,J=6.8Hz), 7.76(2H,d,J=7.3Hz), 8.12(1H,s), 8.45(1H,s)

$N^6$-(9-xanthenyl)methyl-2'-O-methyladenosine (Compound 29) NMR($D_2O$): δ=3.32(3H,s), 3.61(2H,m), 3.69(1H,m), 4.00(1H,m), 4.36(4H,m), 5.31(1H,d,J=3.9Hz), 5.43(1H,m), 6.04(1H,d,J=5.4Hz), 7.00-7.40(8H,m), 8.01(1H,m), 8.20(1H,s), 8.43(1H,s)

EXAMPLE 2

50 g of 5-aminoimidazol-4-carboxamide-1-ribofuranoside was dissolved in 2 l of ethanol solution of sodium ethoxide. 20 ml of ethyl acetate was added, and the reaction mixture was heated for 3 hours at 120° C. After cooling, 1 l of water was added. The solution was neutralized by ion-exchange resin and concentrated to dryness. 200 ml of acetic anhydride and 250 ml of pyridine were added and the solution was stirred at room temperature. The solution was concentrated to dryness and the residue was separated with chloroform/water. The chloroform layer was washed with 0.1 N hydrochloric acid aqueous solution, saturated aqueous solution of sodium hydrogencarbonate and brine, and then dried over sodium sulfate anhydride.

And in the same manner as Example 1 (ii) to (v), 6-chloro-2-methyl-9-(2'-O-methyl-β-D-ribofuranosyl)-9H-purine was obtained.

The resulting product and aminocyclohexane were reacted in the same manner as Example 1 (vi) to give $N^6$cyclohexyl-2,2'-O-dimethyladenosine (Compound 30).

NMR($D_2O$): δ=1.33(4H,m), 1.61(2H,,m), 1.74(2H,m), 1.87(2H,m), 2.40(3H,s), 3.28(3H,s), 3.57(1H,m), 3.67(1H,m), 4.00(1H,m), 4.09(1H,m), 4.34(2H,m), 5.26(1H,d,J=4.39Hz), 5.75(1H,m), 5.96(1H,d,J=6.35Hz), 2.51(1H,m), 8.26(1H,s)

The following descriptions serve to illustrative pharmaceutical studies of the compounds of the present invention.

(1) Acute toxicity test

The test compounds of the present invention, which were dissolved or suspended in 0.5% carboxymethylcellulose (C.M.C.) aqueous solution, were orally administered to groups of 2 to 5 ddY-strain male mice, and the $LD_{50}$ values were calculated based on the death rate for 14 days thereafter. An example of the results is shown in Table 1.

TABLE 1

| Test Compound | $LD_{50}$ (mg/kg) |
|---|---|
| Compound 8 | 230 |
| Compound 11 | 450 |
| Compound 16 | 230 |
| Compound 24 | 250 |

(2) Antihypertensive activity

The test compounds, which were dissolved or suspended in 0.5% C.M.C. aqueous solution, were orally administered to groups of 3 spontaneously hypertensive rats (SHR), 33 to 36 weeks old, which were fasted for 20 hours before drug administration. Blood pressure was measured before and 2 hours after the administration of the test drug. An example of the results is shown in Table 2 and FIG. 1. Data show the mean value ±S.E.

TABLE 2

| Test Compound | Dosage (mg/kg) | Blood pressure (mmHg) Before | 2 hrs | (Decrease %) |
|---|---|---|---|---|
| Control | — | 223 ± 3 | 221 ± 6 | (0.9 ± 2.6) |
| Compound 1 | 0.3 | 228 ± 12 | 98 ± 8 | (56.5 ± 5.5) |
| Compound 2 | 0.3 | 206 ± 12 | 129 ± 8 | (37.5 ± 1.7) |
| Compound 5 | 3 | 211 ± 5 | 148 ± 19 | (30.0 ± 8.4) |
| Compound 8 | 3 | 206 ± 4 | 140 ± 7 | (36.2 ± 5.7) |
| Compound 11 | 3 | 225 ± 11 | 133 ± 21 | (41.3 ± 7.0) |
| Compound 12 | 10 | 213 ± 12 | 164 ± 5 | (22.7 ± 2.2) |
| Compound 16 | 3 | 206 ± 1 | 109 ± 9 | (47.2 ± 4.2) |
| Compound 17 | 3 | 219 ± 3 | 187 ± 7 | (14.5 ± 1.9) |
| Compound 24 | 1 | 218 ± 7 | 98 ± 15 | (55.4 ± 5.6) |

As shown by the above-mentioned results, the adenosine derivatives of the present invention have excellent hypotensive effects at a slight amount of dosage. Furthermore, as shown by FIG. 1, the compounds of the invention, in which characteristically 2-position of sugar part of adenosine is O-alkylated, have longer hypotensive effects compared to the characterless adenosine derivatives which is not O-alkylated. Hypotensive activities of the present invention are kept for long time, so that they have the advantage of cutting down on taking time of drug administration.

Thus the compounds of the present invention have excellent antihypertensive effect at oral administration and do not have severe side effect such as bradycardia. Therefore, the compounds of the present invention are not only useful as antihypertensive drugs for oral administration, but also as drugs for various diseases caused by hypertension, e.g., cerebrovascular disease such as cerebral hemorrhage, cerebral infarction or subarachnoidal hemorrhage, cardiopathy such as congestive heart failure, myocardial infarction or sudden cardiac death, and renal insufficiency.

The compounds of the present invention can be made into pharmaceutical compositions by combination with appropriate medicinal carriers or diluents, and can be formulated into preparations in solid, semisolid, liquid or gaseous form such as tablets, capsules, powders, granules, solutions, suppositories, injections and cataplasms in usual ways for oral or parenteral administrations.

In pharmaceutical dosage forms, the compounds of the present invention can be used in the form of their pharmaceutically acceptable salts, and also can be used alone or in appropriate association, as well as in combination with other pharmaceutically active components.

In case of oral preparations, the compounds can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, the compounds of the invention can be made into a suppository by mixing with a variety of bases, e.g. fatty and oily base such as cacao butter, emulsifying base or water-soluble base such as macrogol.

The compounds of the present invention can be formulated into a preparations for injections by dissolving, suspending or emulsifying in aqueous or nonaqueous solvent, such as distilled water for injection, physiologically saline solution, vegetable oil, synthetic aliphatic acid glycerides, esters of higher aliphatic acid or propylene glycol.

Cataplasms can be prepared by mixing the compounds with mentha oil, concentrated glycerin, kaolin or other suitable additives.

The desirable dose of the compounds of the present invention varies with the subject, form of the drug, method and period of administration. However, in order to obtain desirable effects, generally it is recommended to administer orally 0.1 to 1,000 mg, preferably 0.2 to 500 mg daily. Unit preparations are also recommended for administration in one to several units daily.

In case of parenteral administrations e.g. injections, doses of the compounds in the order of one tenth to one second of the above dose are preferable as daily doses.

Some prescriptions of the pharmaceutical compositions are shown below as examples which contain the compounds of the present invention as active ingredients.

Prescription example 1 (tablet)

| Component | Content in a tablet (mg) |
|---|---|
| compound of this invention | 5 |
| lactose | 145 |
| corn starch | 40 |
| magnesium stearate | 10 |
| Total | 200 mg |

Prescription example 2 (capsule)

| Component | Content in a capsule (mg) |
|---|---|
| compound of this invention | 10 |
| lactose | 240 |
| Total | 250 mg |

Prescription example 3 (injection)

| Component | Content in an ampule (mg) |
|---|---|
| compound of this invention | 5 |
| sodium chloride | proper amount |
| distilled water for injection | proper amount |
| Total | 1 ml |

What is claimed is:

1. An adenosine compound of the formula (I):

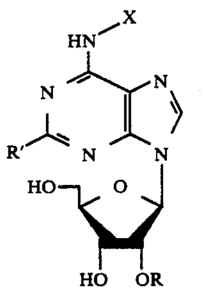

(I)

wherein R is a $C_{1-3}$ alkyl group; R' is hydrogen or a $C_{1-3}$ alkyl group; X is a $C_{3-8}$ cycloalkyl group, a $C_{1-4}$ alkyl group having one or two hydroxy groups, a $C_{1-3}$ group havine one or two phenyl groups, a bicycloheptyl group, a $C_{1-3}$ alkyl group having a naphthyl group, a $C_{1-3}$ alkyl group having an acenaphthylenyl group, or a group of the formula (II) or (III);

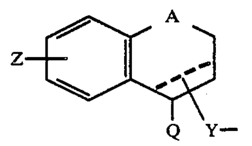
(II)

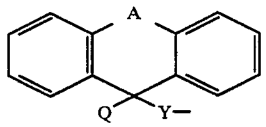
(III)

wherein Z is hydrogen, a hydroxy group or a $C_{1-3}$ alkoxy group, Q is hydrogen or a hydroxy group, A is —$CH_2$—, —o—, —s— or shows a direct connection; Y is —$(CH_2)_n$— or shows a direct connection; n is an integer of 1 to 3; and the broken line represents the presence or absence of a second bond, or a pharmaceutically acceptable salt thereof.

2. An adenosine compound or a salt thereof according to claim 1 wherein R' is hydrogen.

3. A pharmaceutical composition comprising as an active ingredient an effective amount of an adenosine compound or salt thereof of claim 1, together with a pharmaceutically acceptable carrier.

4. A method for treating hypertension in a mammal which comprises administering to the mammal an antihypertensive effective amount of at least one adenosine compound or pharmaceutically acceptable salt thereof of claim 1.

* * * * *